US00PP32297P2

(12) United States Plant Patent
Olesen

(10) Patent No.: US PP32,297 P2
(45) Date of Patent: Oct. 13, 2020

(54) MINIATURE ROSE PLANT NAMED 'POULPAR114'

(50) Latin Name: ***Rosa* hybrid**
Varietal Denomination: Poulpar114

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,257

(22) Filed: Sep. 4, 2019

(51) Int. Cl.
*A01H 5/02* (2018.01)
*A01H 6/74* (2018.01)

(52) U.S. Cl.
USPC ..... Plt./122
CPC ..... *A01H 6/749* (2018.05)

(58) Field of Classification Search
USPC ..... Plt./122
CPC ..... A01H 6/749; A01H 5/02
See application file for complete search history.

*Primary Examiner* — Keith O. Robinson

(57) ABSTRACT

A new garden rose plant of the miniature class which has abundant, red flowers and attractive foliage. This new and distinct variety has shown to be uniform and stable in the resulting generations from asexual propagation.

2 Drawing Sheets

Botanical designation: *Rosa* hybrid.
Variety denomination: 'Poulpar114'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulpar114', originated as a single seedling from the stated cross.

The new variety may be distinguished from its male pollen parent and female seed parent primarily by the following characteristics. The male pollen parent plant has a growth height of 40 cm, while the new variety has a growth height of 25 to 35 cm. The female seed parent plant has Red Group 46A flowers while the new variety has Red Group 46B flowers.

The objective of the hybridization of this rose variety was to create a new and distinct variety with unique qualities, such as:

1. Uniform and abundant red flowers;
2. Vigorous, but compact growth when propagated on its own roots;
3. Exceptional disease resistance.

This combination of qualities is not present in previously available commercial cultivars of this type, known to the inventor, and distinguish 'Poulpar114' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulpar114' was selected in the spring of 2013 by the inventor as a single plant from the progeny of the aforementioned hybridization.

Asexual reproduction of 'Poulpar114' by rooted cuttings was first done by Mogens N. Olesen in the nursery in Fredensborg, Denmark in July, 2013. This initial and other subsequent asexual propagations conducted in controlled environments have demonstrated that the characteristics of 'Poulpar114' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpar114'.

Specifically illustrated in FIG. 1 of the drawings are open flowers, petals detached, sepals detached revealing reproductive flower parts.

Figure 2:
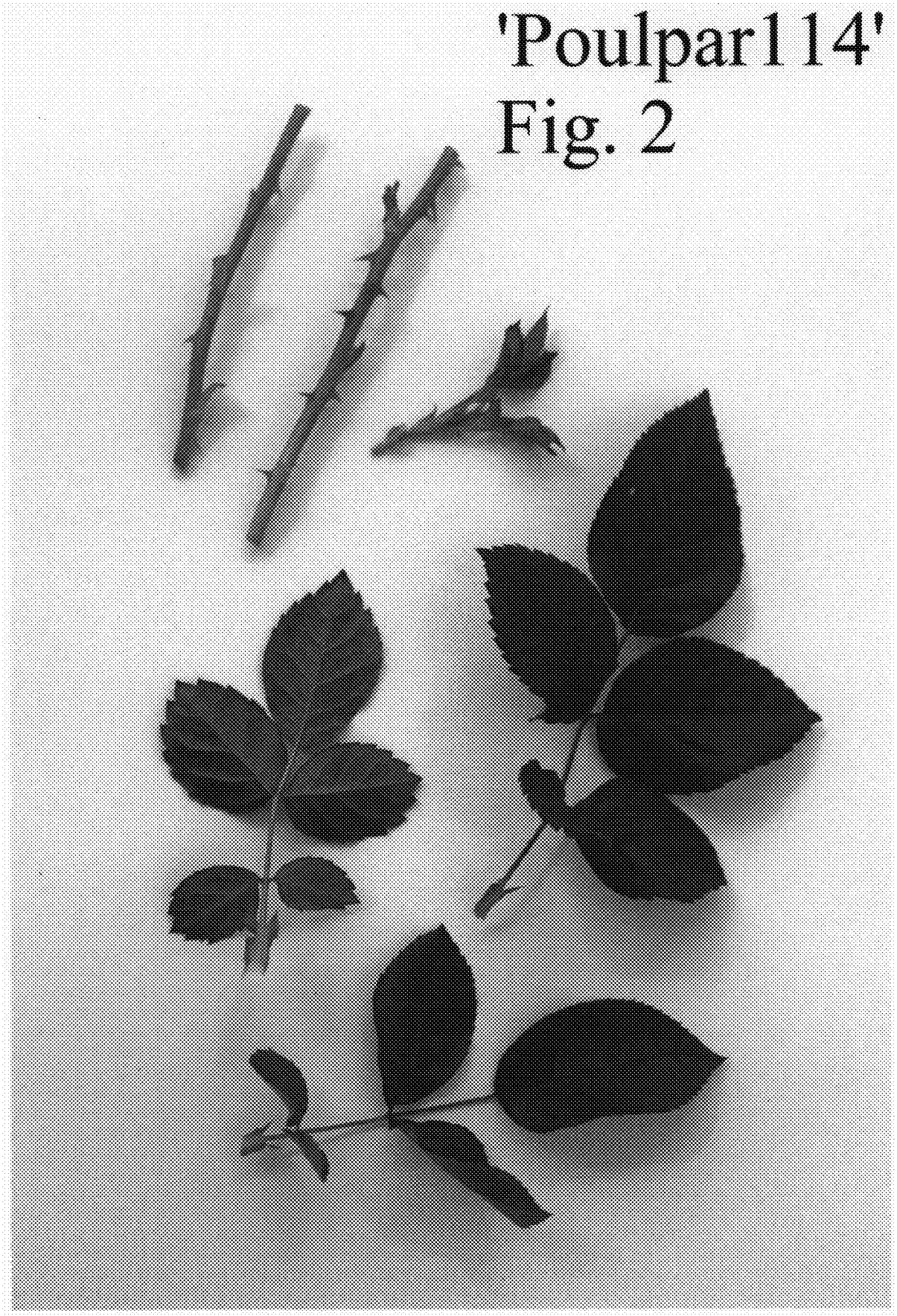

Specifically illustrated in FIG. 2 of the drawings are mature and juvenile leaves, and bare stems. Plants shown are 2 years of age.

DETAILED DESCRIPTION OF THE VARIETY

The following is a description of 'Poulpar114', as observed in its growth in a glasshouse in Odense Denmark, in 24 cm containers. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulpar029', U.S. Plant Pat. No. 16,148 are compared to 'Poulpar114' in Chart 1.

CHART 1

| | 'Poulpar114' | 'Poulpar029' |
|---|---|---|
| Petal Count | 35 petals | 30 petals |
| Flower Diameter | 65 mm | 35 mm |
| General Tonality of Flower Color | Red Group 46B | Red Group 53A |

FLOWER AND FLOWER BUD

Blooming habit: Continuous.

Flower bud:

*Size*.—Upon opening, 21 mm in length from base of receptacle to end of bud. Bud diameter is 12 mm.

*Bud form*.—Ovoid.

*Bud color*.—As sepals divide petals are Red Group 53A.

*Sepal inner surface*.—Color: Yellow-Green Group 146B. Surface: Lightly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have no foliaceous appendages.

*Sepal size*.—26 mm long, 5 mm wide.

*Receptacle*.—Texture: Smooth. Size: 10 mm in height, 8 mm wide. Color: Yellow-Green Group 144A. Shape: Funnel.

*Pedicel*.—Surface: Somewhat rough with small prickles. Length: 75 mm. Diameter: 3 mm on average. Color: Yellow-Green Group 144A. Strength: Strong.

Flower bud development: Flower buds are borne in clusters of 3 flower buds per stem, on average.

Flower bloom:

*Fragrance*.—Light floral scent.

*Duration*.—The blooms have a duration on the plant of approximately 21 days. Petals fall cleanly away from plant after flowers have fully matured.

*Size*.—Flower diameter is 65 mm when open. Flower depth is 21 mm.

*Flower shape*.—High centered, double, with a high pointed center which is tightly closed.

*Shape of flower, side view*.—The upper portion is rounded. The lower portion is flat concave.

Petalage: Under normal conditions, flowers have about 35 petals.

General tonality of flower: Open flowers are Red Group 46B. The color does not change as flowers mature.

Petal color:

*Outer petals*.—Upper surface: A blend fo Red Group 46B and Red Group 46A with occasional streaks the color of Red Group 55B. Lower surface: Red Group 53C.

*Inner petals*.—Upper surface: A blend fo Red Group 46B and Red Group 46A with occasional streaks the color of Red Group 55B. Lower surface: Red Group 53C.

*Basal petal spots, upon opening*.—Upper surface: Yellow Group 6B. Lower surface: Yellow Group 4C.

Petals:

*Petal reflex*.—Strong reflex.

*Margin*.—Entire and uniform no undulation.

*Shape*.—Broad and elliptic. Apex shape: Rounded. Base shape: Rounded.

*Size*.—27 mm (l)×35 mm (w).

*Texture*.—Smooth.

*Thickness*.—Average.

Petaloids:

*Size*.—15 mm (l) by 15 mm (w).

*Quantity*.—About 5.

*Shape*.—Elliptical with an acute base and rounded apices.

*Margins*.—Entire.

*Color*.—The upper petaloid surface is Red Group 46B with occasional streaks the color of Red Group 55B. At the base of the upper side, Yellow Group 6B. The lower surface is Red Group 53C with basal intonation of Yellow Group 4C.

Reproductive flower parts:

*Pollen*.—None observed.

*Anthers*.—Size: 2 mm in length. Color: Yellow Group 12C. Quantity: 38 on average.

*Filaments*.—Color: Yellow Group 12A and Orange-Red Group 34C. Length: 12 mm.

*Pistils*.—Length: 8 mm. Quantity: 23 on average.

*Stigmas*.—Color: White Group 155A.

*Styles*.—Color: White Group 155A.

*Location of stigmas*.—Superior in location relative to the length of the filaments and the height of the anthers.

*Hips*.—None Observed.

PLANT

Plant growth: Upright, bushy. Plants are 25 to 35 cm in height, and 25 cm wide.

Stems:

*Color of juvenile growth*.—Yellow-Green Group 144B.

*Color of mature growth*.—Yellow-Green Group 144A.

*Length*.—Canes are about 10 cm from the base of the plant to the flowering portion.

*Diameter*.—About 5 mm.

*Internodes*.—On mature canes about 45 mm between nodes.

*Surface texture*.—Young wood: Smooth. Older wood: Smooth.

Long prickles:

*Incidence*.—About 11 prickles per 10 cm of stem.

*Size*.—Average length of prickles on mature stems is 6 mm.

*Shape*.—Upper portion is linear. Lower portion is concave.

*Color*.—Juvenile prickles: Greyed-Yellow Group 160D with intonations of Greyed-Red Group 179C. Mature prickles: Greyed-Red Group 181B.

Plant foliage:

*Compound leaf*.—150 to 160 mm (l)×110 (w).

*Quantity*.—2 leaves per 10 cm of stem on average.

*Leaf bearing angle to the stem*.—45 degrees.

*Color of juvenile foliage*.—Upper side: Yellow-Green Group 146A. Lower side: Yellow-Green Group 147B with intonations of Greyed-Red Group 181B.

*Color of mature foliage*.—Upper side: Yellow-Green Group 147A. Lower side: Yellow-Green Group 147B.

Plant leaves and leaflets:

*Stipules*.—Size: 12 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 30 mm. Diameter: 2 mm. Upper surface color: Yellow-Green Group 147B. Lower surface color: Yellow-Green Group 144B.

*Rachis*.—Length: 50 mm. Upper surface color: Yellow-Green Group 147B with intonations of Greyed-Red Group 181B. Lower surface color: Yellow-Green Group 144B.

*Leaflet*.—Quantity: Normally 5 leaflets. Margins: Serrated. Size: Terminal leaflets are about 73 mm long, 46 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpar114', substantially as illustrated and described herein, due to its abundant red flowers, disease resistance, and extended period of bloom.

* * * * *

Figure 1:
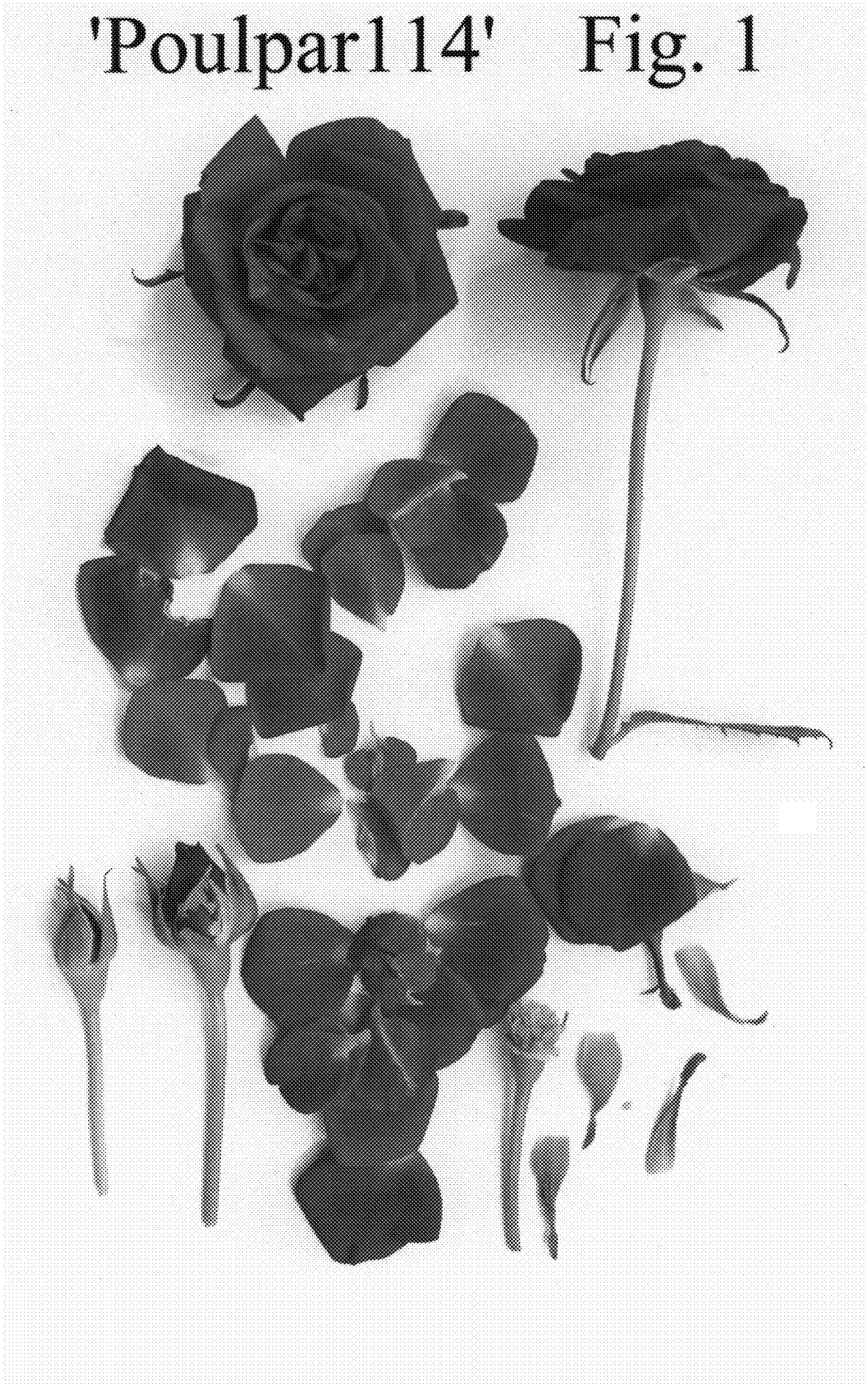

'Poulpar114' Fig. 1

'Poulpar114'